United States Patent

Buchecker et al.

[11] Patent Number: 5,413,734
[45] Date of Patent: May 9, 1995

[54] 4-CYANO-3-FLUOROPHENYL ESTERS

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 250,393

[22] Filed: May 27, 1994

Related U.S. Application Data

[63] Continuation of Ser. No. 57,424, May 18, 1993, abandoned, which is a continuation of Ser. No. 718,487, Jun. 20, 1991, abandoned.

[30] Foreign Application Priority Data

Jul. 6, 1990 [CH] Switzerland ............... 2254/90

[51] Int. Cl.$^6$ ............... C09K 19/06; C09K 19/34; C09K 19/30; G02F 1/13
[52] U.S. Cl. ............... 252/299.6; 252/299.61; 252/299.63; 252/299.67; 359/103
[58] Field of Search ............ 252/299.61, 299.67, 252/299.63, 299.6

[56] References Cited

U.S. PATENT DOCUMENTS

| | | | |
|---|---|---|---|
| 4,424,371 | 1/1984 | Hsu | 549/373 |
| 4,521,327 | 6/1985 | Demus et al. | 252/299.61 |
| 4,550,981 | 11/1985 | Petrzilka et al. | 359/103 X |
| 4,551,280 | 11/1985 | Sasaki et al. | 558/416 X |
| 4,565,425 | 1/1986 | Petrzilka et al. | 359/103 X |
| 4,621,901 | 11/1986 | Petrzilka et al. | 359/103 X |
| 4,708,441 | 11/1987 | Petrzilka et al. | 359/103 X |
| 4,756,847 | 7/1988 | Yoshida et al. | 252/299.61 |
| 4,770,503 | 9/1988 | Buchecker et al. | 359/103 X |
| 4,818,428 | 4/1989 | Scheuble et al. | 252/299.1 |
| 4,886,621 | 12/1989 | Sage et al. | 252/299.61 |
| 5,013,478 | 5/1991 | Petrzilka et al. | 252/299.63 |
| 5,286,410 | 2/1994 | Weber et al. | 252/299.61 |

FOREIGN PATENT DOCUMENTS

| | | |
|---|---|---|
| 359146 | 9/1989 | European Pat. Off. |
| 3334054 | 9/1982 | Germany |
| 3302218 | 1/1983 | Germany |
| 3447359 | 12/1984 | Germany |
| 3315633 | 5/1985 | Germany |
| 252828 | 9/1986 | Germany |
| 2225444 | 9/1990 | Japan |
| 86/4081 | 7/1986 | WIPO |
| 8809360 | 12/1988 | WIPO |
| 9112294 | 1/1991 | WIPO |

OTHER PUBLICATIONS

Derwent abstract of EP 359,146.
Derwent abstract of DE 3,515,633.
Derwent abstract of DD 252,828.
English Abstract of Japanese Patent Application No. 200 429/1984.

*Primary Examiner*—Robert L. Stoll
*Assistant Examiner*—C. Harris
*Attorney, Agent, or Firm*—George M. Gould; George W. Johnston; Robert A. Silverman

[57] ABSTRACT

Compounds of the formula

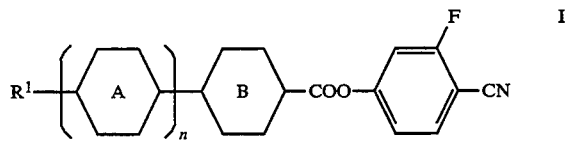

wherein ring A is trans-1,4-cyclohexylene, 1,4-phenylene, pyrimidine-2,5-diyl or trans-1,3-dioxane-2,5-diyl; n is either 0 or 1; ring B stands for 1,4-phenylene or trans-1,4-cyclohexylene; and $R^1$ is 3E-alkenyl or on a saturated ring also 1E-alkenyl, their manufacture, liquid crystalline mixtures which contain these compounds as well as their use for electro-optical purposes.

11 Claims, No Drawings

4-CYANO-3-FLUOROPHENYL ESTERS

This is a continuation of application Ser. No. 08/057,424, filed May 18, 1993, now abandoned, which is a Rule 62 Continuation of Ser. No. 07/718,487, filed Jun. 20, 1991, now abandoned.

BACKGROUND OF THE INVENTION

1. Field

The present invention is concerned with novel 4-cyano-3-fluorophenyl esters, their manufacture, liquid crystalline mixtures which contain these compounds as well as their use for electro-optical purposes.

2. Discussion

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells having a "twisted nematic" structure, STN cells ("super-twisted nematic"), SBE cells ("super-birefringence effect") and OMI cells ("optical mode interference"). The most common indicating devices are based on the Schadt-Helfrich effect and have a twisted nematic structure.

Liquid crystals must have a good chemical and thermal stability and a good stability towards electric fields and electro-magnetic radiation. Moreover, liquid crystals should have a low viscosity and in the cells should give short response times, a low threshold potential and a high contrast. They should have a suitable mesophase, for example a nematic or cholesteric mesophase for the aforementioned cells. Other properties such as the electrical conductivity, the dielectric anisotropy and the optical anisotropy must fulfil different requirements depending on the type of cell.

Liquid crystals are generally used as mixtures, because the properties which are desired for the respective application can be optimized by mixing different components. It is therefore important that the components have a good miscibility with one another.

SUMMARY OF THE INVENTION

The present invention provides compounds of the formula

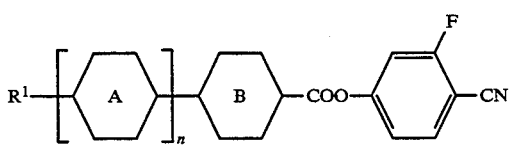

wherein ring A is trans-1,4-cyclohexylene, 1,4-phenylene, pyrimidine-2,5-diyl or trans-1,3-dioxane-2,5-diyl; n is either 0 or 1; ring B stands for 1,4-phenylene or trans-1,4-cyclohexylene; and $R^1$ is 3E-alkenyl or on a saturated ring also 1E-alkenyl.

The compounds of formula I are liquid crystals which have a surprisingly broad mesophase range and comparatively high clearing points. They have a good miscibility with usual liquid crystal materials. Further, they have a high positive dielectric anisotropy and a correspondingly low threshold potential. The compounds in accordance with the invention are well suited as components of nematic and cholesteric mixtures and, by virtue of their good solubility, can be used in comparatively high concentrations. Having regard to their high dielectric anisotropy, they lower the threshold potential in mixtures without restricting the mesophase.

The properties of the compounds of formula I can be varied to a certain degree depending on the number and significance of the rings. For example, aromatic rings lead to higher values of the optical anisotropy and saturated rings lead to lower values of the optical anisotropy and rings such as pyrimidine-2,5-diyl and trans-1,3-dioxane-2,5-diyl influence the dielectric anisotropy.

Moreover, compounds of formula I in which n =1 are characterized by high clearing points.

DETAILED DESCRIPTION OF THE INVENTION

The present invention concerns compounds of the formula

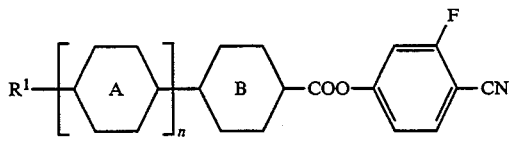

wherein ring A is trans-1,4-cyclohexylene, 1,4-phenylene, pyrimidine-2,5-diyl or trans-1,3-dioxane-2,5-diyl; n is either the integer 0 or 1; ring B is 1,4-phenylene or trans-1,4-cyclohexylene; and $R^1$ is 3E-alkenyl or when positioned on a saturated ring, $R^1$ also can be 1E-alkenyl.

The compounds of formula I are liquid crystals which have a surprisingly broad mesophase range and comparatively high clearing points. They have a good miscibility with usual liquid crystal materials. Further, they have a high positive dielectric anisotropy and a correspondingly low threshold potential. The compounds in accordance with the invention are well suited as components of nematic and cholesteric mixtures and, by virtue of their good solubility, can be used in comparatively high concentrations. Having regard to their high dielectric anisotropy, they lower the threshold potential in mixtures without restricting the mesophase.

The properties of the compounds of formula I can be varied to a certain degree depending on the number and significance of the rings. For example, aromatic rings lead to higher values of the optical anisotropy and saturated rings lead to lower values of the optical anisotropy and rings such as pyrimidine-2,5-diyl and trans-1,3-dioxane-2,5-diyl influence the dielectric anisotropy. Moreover, compounds of formula I in which n is 1 are characterized, by high clearing points.

Unless otherwise stated, "alkyl" is a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched-chain alkyl groups are isopropyl, isobutyl, sec-butyl, 1-methylbutyl, 2-methylbutyl, 3-methylpentyl, 4-methylhexyl and isopentyl. "Lower alkyl" is straight-chain and branched-chain alkyl groups of 1 to 5 carbon atoms.

The term "alkoxy" as well as any other groups in the specification containing "alkyl" are moieties in which their "alkyl" portions are as defined previously.

The term "alkenyl" is straight-chain or branched-alkenyl residues of 2–12 carbon atoms. More particularly, the term "1E-alkenyl" embraces straight-chain or branched alkenyl residues of 2–12 carbon atoms, with the double bond positioned between the first and second carbons atom and being the E geometric isomer. The term "1E-alkenyl" thus embraces straight-chain and branched alkenyl groups such as, for example, vinyl, 1E-propenyl, 1E-butenyl, 1E-pentenyl, 1E-hexenyl, 1E-heptenyl, 1E-octenyl and the like. The terms "2E-alkenyl", "3E-alkenyl" etc. are analogously defined. The term "3E-alkenyl" thus embraces straight-chain and branched alkenyl groups such as, for example, 3-butenyl, 3E-pentenyl, 3E-hexenyl, 3E-heptenyl, 3E-octenyl and the like.

The term "4-alkenyl" is an alkenyl group of 5–12 carbon atoms with the double bond positioned between the fourth and fifth carbon atoms, including either or both of the E and Z geometric isomers. The terms "3-alkenyl", "2-alkenyl", etc. are analogously defined. The term "3-alkenyloxy" is an alkenyloxy group of 4–12 carbon atoms with the double bond positioned between the third and fourth carbon atoms, including either or both E and Z geometric isomers.

The term "pyrimidine-2,5-diyl" is a pyrimidine ring which is substituted in the 2- and 5-position. The term "trans-1,3-dioxane-2,5-diyl" is a 1,3-dioxane ring which is substituted in the 2- and 5-position and in which the substituents are trans to each other. A pyrimidine or 1,3-dioxane ring present as ring A in formula I above can be linked with ring B in the 2- or 5-position, preferably in the 2-position.

The term "saturated ring" is trans-1,4-cyclohexylene and trans-1,3-dioxane-2,5-diyl.

Formula I embraces especially compounds of the formula

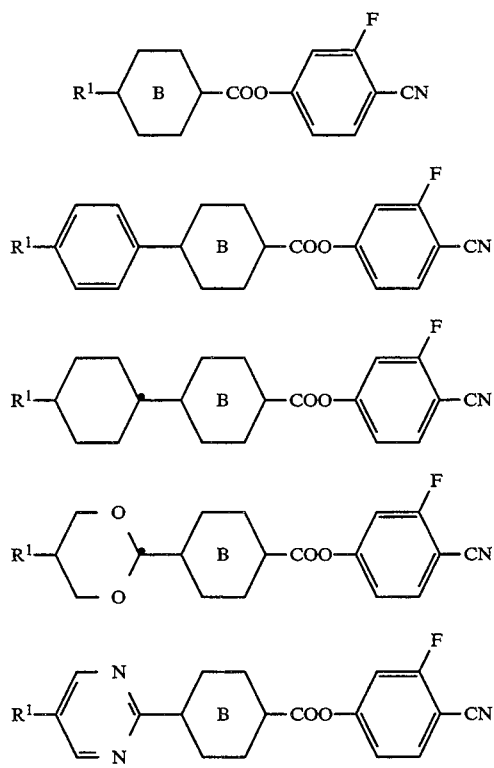

wherein $R^1$ and ring B have the aforementioned significances.

Preferably, ring B in formula I and Ia–Ie is 1,4-phenylene.

Preferably, in each of formula I and Ia–Ie above $R^1$ has a maximum of 12 carbon atoms, with especially preferred residues $R^1$ being those having up to 7 carbon atoms, particularly those having up to 5 carbon atoms such as, for example, 3-butenyl and 3E-pentenyl and the like or on a saturated ring also vinyl, 1E-propenyl, 1E-butenyl, 1E-pentenyl and the like.

The compounds of formula I can be manufactured in accordance with the invention by esterifying an acid of the formula

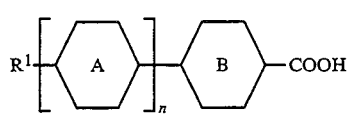

wherein ring A, ring B, $R^1$ and n have the significance given above, or a suitable derivative of this acid with 4-cyano-3-fluorophenol. The esterification of an acid of formula II or of a suitable derivative thereof, for example an acid halide, acid ester, anhydride or the like, can be effected in a manner known per se. Preferably, an acid of formula II can be reacted with 4-cyano-3-fluorophenol in the presence of N,N'-dicyclohexylcarbo-diimide and 4-(dimethylamino)pyridine in a known manner, for example as described in EP-A-0122389 (U.S. Pat. No. 4,565,425).

The acids of formula II are known or can be prepared, for example, from known nitriles by hydrolysis (EP-A-0122389 and EP-A-0167912) (U.S. Pat. No. 4,621,901).

The invention is also concerned with liquid crystalline mixtures having at least two components, of which at least one component is a compound of formula I.

By virtue of their relatively high dielectric anisotropies, the compounds of formula I bring about in the liquid crystalline mixtures in accordance with the invention a lowering of the threshold potential without restricting the nematic range. The compounds of formula I in accordance with the invention are especially suitable for nematic mixtures having a high positive dielectric anisotropy and, insofar as at least one component is optically active, also for cholesteric mixtures having a positive dielectric anisotropy. They are suitable above all for use in cells having a twisted nematic liquid crystal structure, especially for STN cells.

Having regard to the good solubility of the compounds of formula I and having regard to their good miscibility with one another, their content in the mixtures in accordance with the invention can be relatively high. In general, however, a content of 1–50 wt. %, especially about 5–30 wt. %, of compounds of formula I is preferred.

A preferred aspect is concerned with mixtures which contain, in addition to one or more compounds of formula I, one or more compounds of the formula

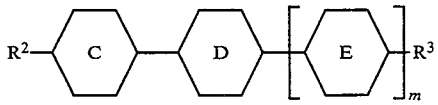

wherein rings C, D and E each independently are 1,4-phenylene, trans-1,4-cyclohexylene or one of the rings also can be pyrimidine-2,5-diyl; m is either the integer 0 or 1; $R^2$ is alkyl, alkoxyalkyl, 3E-alkenyl, 4-alkenyl or when positioned on trans-1,4-cyclohexylene, $R^2$ also can be 1E-alkenyl; and $R^3$ is cyano, alkyl, alkoxy, alkoxyalkyl, 3E-alkenyl, 4-alkenyl, 2E-alkenyloxy, 3-alkenyloxy or when positioned on trans-1,4-cyclohexylene, $R^3$ also can be 1E-alkenyl, and at least one compound of the formula

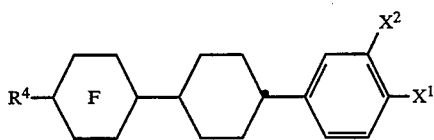  IV wherein ring F is trans-1,4-cyclohexylene or trans-1,3-dioxane-2,5-diyl; $R^4$ is alkyl, 1E-alkenyl, 3E-alkenyl, 4-alkenyl or alkenyloxy; $X^1$ is fluorine or chlorine; and $X^2$ is hydrogen or fluorine.

Preferably, these liquid crystalline mixtures can contain, in addition to one or more compounds of formula I, an amount of one or more compounds of formula III, which is preferably 20–80% (weight %). An amount of one or more compounds of formula III of 40–60% is especially preferred. The liquid crystalline mixtures can contain, in addition to one or more compounds of formula I as well as one or more compounds of formula III, an amount of one or more compounds of formula IV. This amount is preferably 5–25%, particularly 10–20%.

Other compounds which are excellently suited for use in mixtures with the compounds in accordance with the invention are compounds of the formula

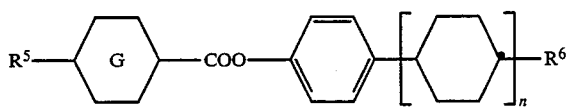  V

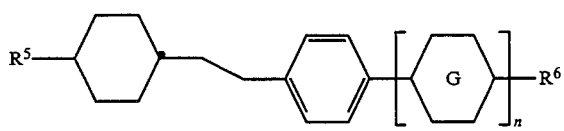  VI

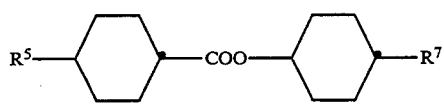  VII

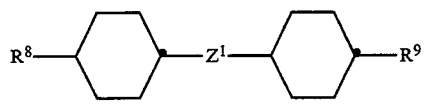  VIII

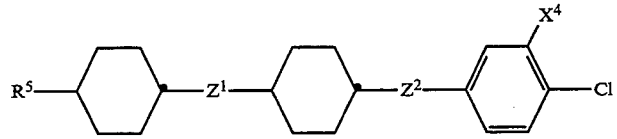  IX

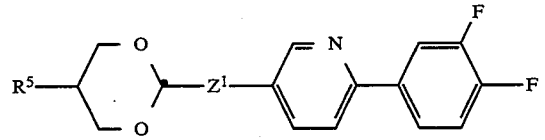  X

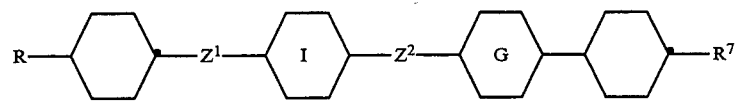  XI

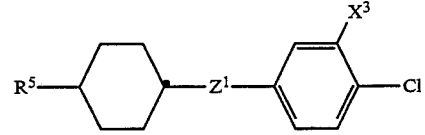  XII

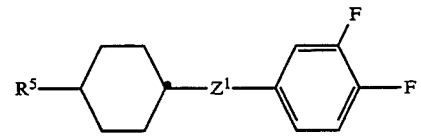  XIII

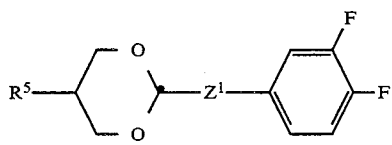 XIV

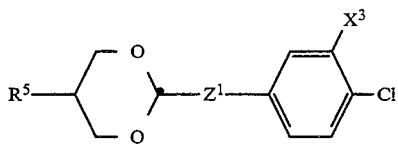 XV

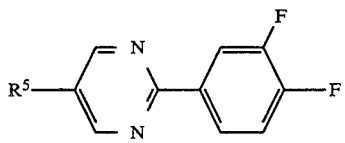 XVI

 XVII

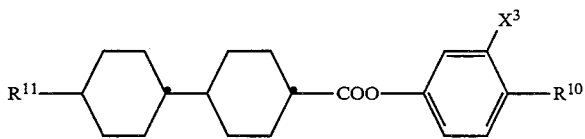 XVIII

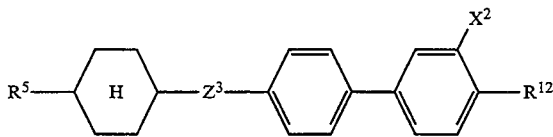 XIX wherein n is the integer 0 or 1; $R^5$ and $R^7$ each independently are alkyl, alkoxyalkyl, 3E-alkenyl, 4-alkenyl or when positioned on a saturated ring $R^5$ and $R^7$ each independently can be 1E-alkenyl; $R^6$ is alkyl, 3E-alkenyl, 4-alkenyl or when positioned on a cyclohexane ring, $R^6$ also can be 1E-alkenyl or when positioned on a benzene ring, $R^6$ also can be cyano, isothiocyanato, alkoxy, 2E-alkenyloxy or 3-alkenyloxy; ring G is 1,4-phenylene or trans-1,4-cyclohexylene; $R^8$ is alkyl, 1E-alkenyl, 3E-alkenyl or 4-alkenyl; $Z^1$ and $Z^2$ each are a single covalent bond or ethylene, with the provision that two aromatic rings only are joined by a single bond; $R^9$ is cyano, alkyl, 1E-alkenyl, 3E-alkenyl, 4-alkenyl alkoxy, 2E-alkenyloxy, 3-alkenyloxy, alkoxymethyl or (2E-alkenyl)oxymethyl; ring I is 1,4-phenylene, trans-1,4-cyclohexylene, pyridine-2,5-diyl, pyrimidine-2,5-diyl or trans-1,3-dioxane-2,5-diyl; ring H is trans-1,4-cyclohexylene or trans-1,3-dioxane-2,5-diyl; $R^{10}$ is fluorine, chlorine or cyano; $R^{11}$ is alkyl, 1E-alkenyl, 3E-alkenyl or 4-alkenyl, $R^{12}$ is fluorine or chlorine; $X^2$ is hydrogen or fluorine; and $X^3$ is hydrogen, fluorine or chlorine.

The term "saturated ring" embraces trans-1,4-cyclohexylene and trans-1,3-dioxane-2,5-diyl. Residues $R^5$ to $R^9$ and $R^{11}$ each preferably have a maximum of 12 carbon atoms. Straight-chain residues are generally preferred.

The manufacture of the compounds of formula I and of liquid crystalline mixtures containing these compounds are illustrated in more detail by the following Examples. Unless indicated otherwise, the examples were carried out as written. C is a crystalline phase, N is a nematic phase and I is an isotropic phase. $V_{10}$ is the voltage for 10% transmission, $t_{on}$ and $t_{off}$ denote respectively the switching-on time and the switching-off time and $\Delta n$ is the optical anisotropy. The electro-optical properties were measured at 22° C. unless indicated otherwise.

EXAMPLE 1

A suspension of 2.68 g of 4-[trans-4-(1E-propenyl)cyclohexyl]benzoic acid, 1.8 g of 4-cyano-3-fluorophenol and 187 mg of 4-(dimethylamino)pyridine in 25 ml of methylene chloride was cooled to 0° C. and treated while stirring with 3.17 g of N,N'-dicyclohexylcarbodiimide. After stirring at 0° C. for 5 minutes and at room temperature for 3 hours the suspension was filtered and the filtrate was concentrated. Chromatographic purification of the residue on 50 g of basic aluminium oxide with methylene chloride and subsequent crystallization from hexane/ethyl acetate gave 2.67 g of 4-cyano-3-fluorophenyl 4-[trans-4-(1E-propenyl)cyclohexyl]benzoate as colourless crystals; m.p. (C-N) 117.5° C., cl.p. (N—I) 233.1° C.

In an analogous manner there can be manufactured:
4-Cyano-3-fluorophenyl 4-(3-butenyl)benzoate, m.p. (C—I) 68.6° C., cl.p. (N—I) 37° C.,
4-cyano-3-fluorophenyl 4-(3E-pentenyl)benzoate, m.p. (C—I) 64.8° C., cl.p. (N—I) 54.7° C.,
4-cyano-3-fluorophenyl 4-[4'-(3-butenyl)biphenyl]carboxylate, 4-cyano-3-fluorophenyl 4-[4'-(3E-pentenyl)biphenyl]carboxylate,
4-cyano-3-fluorophenyl 4-[trans-4-(3-butenyl)cyclohexyl]benzoate,
4-cyano-3-fluorophenyl 4-[trans-4-(3E-pentenyl)cyclohexyl]benzoate,
4-cyano-3-fluorophenyl 4-[trans-4-vinylcyclohexyl]benzoate,
4-cyano-3-fluorophenyl 4-[trans-4-(3-butenyl)cyclohexyl]benzoate,
4-cyano-3-fluorophenyl 4-[trans-4-(3E-pentenyl)cyclohexyl]benzoate,
4-cyano-3-fluorophenyl 4-[trans-5-vinyl-(1,3-dioxan-2-yl)]benzoate,
4-cyano-3-fluorophenyl 4-[trans-5-(3-butenyl)-(1,3-dioxan-2-yl)]benzoate,
4-cyano-3-fluorophenyl 4-[trans-5-(3E-pentenyl)-2-(1,3-dioxan-2-yl)]benzoate,
4-cyano-3-fluorophenyl 4-[trans-5-(1E-propenyl)-2-(1,3-dioxan-2-yl)]benzoate, m.p. (C-N) 122.6° C., cl.p. (N—I) 242.5° C.,
4-cyano-3-fluorophenyl 4-[5-(3-butenyl)-2-pyrimidyl]benzoate,
4-cyano-3-fluorophenyl 4-[5-(3E-pentenyl)-2-pyrimidyl]benzoate,
4-cyano-3-fluorophenyl trans-4-vinylcyclohexanecarboxylate,
4-cyano-3-fluorophenyl trans-4-(1E-propenyl)cyclohexanecarboxylate,
4-cyano-3-fluorophenyl trans-4-(3-butenyl)cyclohexanecarboxylate,
4-cyano-3-fluorophenyl trans-4-(3E-pentenyl)cyclohexanecarboxylate,
4-cyano-3-fluorophenyl trans-4'-vinylbicyclohexylcarboxylate,
4-cyano-3-fluorophenyl trans-4'-(1E-propenyl)bicyclohexylcarboxylate,
4-cyano-3-fluorophenyl trans-4'-(3-butenyl)bicyclohexylcarboxylate,
4-cyano-3-fluorophenyl trans-4'-(3E-pentenyl)bicyclohexylcarboxylate,
4-cyano-3-fluorophenyl trans-4-[4-(3-butenyl)phenyl]cyclohexanecarboxylate,
4-cyano-3-fluorophenyl trans-4-[4-(3E-pentenyl)phenyl]cyclohexanecarboxylate,
4-cyano-3-fluorophenyl trans-4-[trans-5-vinyl-2-(1,3-dioxan-2-yl)]cyclohexanecarboxylate,
4-cyano-3-fluorophenyl trans-4-[trans-5-(1E-propenyl)-2-(1,3-dioxan-2-yl)]cyclohexanecarboxylate,
4-cyano-3-fluorophenyl trans-4-[trans-5-(3-butenyl)-2-(1,3-dioxan-2-yl)]cyclohexanecarboxylate,
4-cyano-3-fluorophenyl trans-4-[trans-5-(3E-pentenyl)-2-(1,3-dioxan-2-yl)]cyclohexanecarboxylate,
4-cyano-3-fluorophenyl 4-[5-(1E-propenyl)-2-(1,3-dioxan-2-yl)]benzoate, m.p. (C-N) 122.6° C., cl.p. (N—I) 186° C.,
4-cyano-3-fluorophenyl trans-4-[5-(3-butenyl)-2-pyrimidinyl]cyclohexanecarboxylate and
4-cyano-3-fluorophenyl trans-4-[5-(3E-pentenyl)-2-pyrimidinyl]cyclohexanecarboxylate.

The 4-[trans-4-(1E-propenyl)cyclohexyl]benzoic acid used as the starting material was prepared as follows:

A mixture of 2.5 g of 4-[trans-4-(1E-propenyl)cyclohexyl]benzonitrile and 6.22 g of potassium hydroxide in 50 ml of diethylene ethylene glycol was stirred at 180° C. for 2.5 hours, cooled, added to ice-water/methylene chloride and made acid with 25 percent hydrochloric acid. After extracting the product with methylene chloride, repeatedly washing the organic phase and drying over magnesium sulphate the organic phase was evaporated and gave 2.68 g of 4-[trans-4-(1E-propenyl)cyclohexyl]benzoic acid as a colourless solid.

EXAMPLE 2

The properties of the compounds were investigated by preparing binary mixtures with 4-(trans-4-pentylcyclohexyl)benzonitrile and measuring their threshold potential and response times in a TN cell (low bias tilt) with a plate separation of 8 μm; the 2.5-fold value of the threshold potential $V_{10}$ was chosen as the operating voltage. The corresponding data for pure 4-(trans-4-pentylcyclohexyl)benzonitrile were cl.p. (N—I) 54.6° C., $V_{10}=1.62$ V, $t_{on}=30$ ms, $t_{off}=42$ ms, $\Delta n=0.120$.

Mixture A 90 wt. % of 4-(trans-4-pentylcyclohexyl)benzonitrile,
10 wt. % of 4-cyano-3-fluorophenyl 4-[trans-4-(1E-propenyl)cyclohexyl]benzoate
cl.p. (N—I) 64.2° C., $V_{10}=1.46$ V, $t_{on}=31$ ms, $t_{off}=49$ ms.

Mixture B 80 wt. % of 4-(trans-4-pentylcyclohexyl)benzonitrile,
20 wt. % of 4-cyano-3-fluorophenyl 4-[trans-4-(1E-propenyl)cyclohexyl]benzoate
cl.p. (N—I) 76.9° C., $V_{10}=1.45$ V, $t_{on}=41$ ms, $t_{off}=60$ ms.

Mixture C 90 wt. % of 4-(trans-4-pentylcyclohexyl)benzonitrile,
10 wt. % of 4-cyano-3-fluorophenyl (3-butenyl)benzoate
cl.p. (N—I) 50.8° C., $V_{10}=1.24$ V, $t_{on}=35$ ms, $t_{off}=47$ ms,
$\Delta n=0.127$.

Mixture D 80 wt. % of 4-(trans-4-pentylcyclohexyl)benzonitrile,
20 wt. % of 4-cyano-3-fluorophenyl (3-butenyl)benzoate
cl.p. (N—I) 47.3° C., $V_{10}=0.05$ V, $t_{on}=33$ ms, $t_{off}=55$ ms,
$\Delta n=0.129$.

Mixture E 90 wt. % of 4-(trans-4-pentylcyclohexyl)benzonitrile,
10 wt. % of 4-cyano-3-fluorophenyl 4-(3E-pentenyl)benzoate
cl.p. (N—I) 53.2° C., $V_{10}=1.29$ V, $t_{on}=31$ ms, $t_{off}=48$ ms,
$\Delta n=0.126$.

Mixture F 80 wt. % of 4-(trans-4-pentylcyclohexyl)benzonitrile,
20 wt. % of 4-cyano-3-fluorophenyl 4-(3E-pentenyl)benzoate
cl.p. (N—I) 51.9° C., $V_{10}=1.15$ V, $t_{on}=42$ ms, $t_{off}=52$ ms,
$\Delta n=0.132$.

EXAMPLE 3

The use of the compounds in accordance with the invention is exemplified in the following mixtures.

Basic Mixture 1

6.5% of 4-(5-butyl-2-pyrimidinyl)benzonitrile.

7% of 4-[trans-4-(1E-propenyl)cyclohexyl]benzonitrile.
3% of 2-cyano-5-(trans-4-butylcyclohexyl)pyrimidine.
3% of 2-cyano-5-(trans-4-pentylcyclohexyl)pyrimidine.
2% of 2-(trans-4-cyanocyclohexyl)-5-(trans-4-butylcyclohexyl)pyrimidine.
3% of 4-cyano-4'-[trans-4-(1E-propenyl)cyclohexyl]biphenyl.
13% of trans-4-vinyl-trans-4'-pentylbicyclohexyl.
13% of trans-4-(1E-propenyl)-trans-4'-methoxymethylbicyclohexyl.
4% of trans-4-(3E-pentenyl)-trans-4'-ethoxybicyclohexyl.
5% of trans-4-(3E-pentenyl)-trans-4'-methoxybicyclohexyl.
5% of trans-(1E-propenyl)-4'-(p-tolyl)bicyclohexyl.
8% of 4-[trans-4-(3E-pentenyl)cyclohexyl]phenyl-(trans-4-propylcyclohexanecarboxylate.
4% of 5-(trans-4-pentylcyclohexyl)-2-[4-(trans-4-propylcyclohexyl)phenyl]pyrimidine.
4% of 4-cyano-3-fluorophenyl 4-(3-butenyloxyl)benzoate.
3% of trans-4-vinyl-trans-4'-(4-fluorophenyl)bicyclohexyl.
3% of trans-4-(1E-propenyl)-trans-4'-(4-fluorophenyl)bicyclohexyl.
3% of trans-4-(3-butenyl)-trans-4'-(4-fluorophenyl)bicyclohexyl.
5% of 2-[trans-4-(4-fluorophenyl)cyclohexyl]-5-(1E-propenyl)-1,3-dioxane.
5% of trans-4-(3,4-difluorophenyl)-trans-4'-(1E-propenyl)bicyclohexyl.

Basic Mixture 2

2% of 4-(5-butyl-2-pyrimidinyl)benzonitrile.
8% of 4-[trans-4-(1E-propenyl)cyclohexyl]benzonitrile.
6% of 4-[trans-4-(3E-pentenyl)cyclohexyl]benzonitrile.
5% of 4-[trans-4-(1E-butenyl)cyclohexyl]benzonitrile.
5% of trans-4-vinyl-trans-4'-cyanobicyclohexyl.
6.9% of trans-4-(1E-propenyl)-trans-4'-cyanobicyclohexyl.
3% of 2-cyano-5-(trans-4-butylcyclohexyl)pyrimidine.
3% of 2-cyano-5-(trans-4-pentylcyclohexyl)pyrimidine;
6.4% of (p-cyanophenyl)-4-[2-(trans-4-propylcyclohexyl)ethyl]cyclohexylcarboxylate.
11% of trans-4-(3E-pentenyl)-trans-4'-ethoxybicyclohexyl.
11.7% of trans-4-vinyl-trans-4'-pentylbicyclohexyl.
8% of 4-[trans-4-(3E-pentenyl)cyclohexyl]phenyl (trans-4-propylcyclohexanecarboxylate.
3.9% of trans-4-vinyl-4'-(4-fluorophenyl)bicyclohexyl.
3.9% of trans-4-(1E-propenyl)-4'-(4-fluorophenyl)bicyclohexyl.
3.4% of p-fluoro-phenyl 4-[trans-4-(3E-butenyl)cyclohexyl]cyclohexanoate.
6.8% of trans-4-(3,4-difluorophenyl)-trans-4'-(1E-propenyl)bicyclohexyl.
6% of 2-[trans-4-(4-fluorophenyl)cyclohexyl]-5-(1E-propenyl)dioxolane.

Basic Mixture 3

10% of 4-(5-butyl-2-pyrimidinyl)benzonitrile.
6% of 4-[trans-4-(1E-propenyl)cyclohexyl]benzonitrile.
5.5% of 4-cyano-4'-[trans-4-(1E-propenyl)cyclohexyl]biphenyl.
4.5% of 4-cyano-4'-[trans-4-(3E-pentenyl)cyclohexyl]biphenyl.
13% of trans-4-vinyl -trans-4'-pentylbicyclohexyl.
13% of trans-4-(1E-propenyl)-trans-4'-methoxymethylbicyclohexyl.
13% of trans-4-(3E-pentenyl)-trans-4'-ethoxybicyclohexyl.
5% of trans-(1E-propenyl)-trans-4'-(4-tolyl)bicyclohexyl.
4% of 4-[trans-4-(3E-pentenyl)cyclohexyl)-4'-propylbiphenyl.
4% of 5-(trans-4-pentylcyclohexyl)-2-[4-(trans-4-propylcyclohexyl)phenyl]pyrimidine.
7% of 4-cyano-3-fluorophenyl 4-(3-butenyl)benzoate.
3.5% of trans-4-vinyl-trans-4'-(p-fluorophenyl)bicyclohexyl.
3.5% of trans-4-(3-butenyl)-trans-4'-(p-fluorophenyl)bicyclohexyl.
3.0% of trans-4-(1E-propenyl)-trans-4'-(p-fluorophenyl)bicyclohexyl.
5% of trans-4-(3,4-difluorophenyl)-trans-4'-(1E-propenyl)bicyclohexyl.

Mixture Example A 74.63% of basic mixture 1
15.170% of 4-cyano-3-fluorophenyl 4-(3E-pentenyl)benzoate.
10.2% of 4-cyano-3-fluorophenyl 4-(3-butenyl)benzoate.
cl.p. (N—I) 84° C., $V_{10}$=1.3 V, $t_{on}$=30.3 ms, $t_{off}$=53 ms,
$\Delta n$=0.131.

Mixture Example B 74.91% of basic mixture 2
15.1% of 4-cyano-3-fluorophenyl 4-(3E-pentenyl)benzoate.
9.99% of 4-cyano-3-fluorophenyl 4-(3-butenyl)benzoate.
cl.p. (N—I) 82° C., $V_{10}$=1.32 V, $t_{on}$=35.5 ms, $t_{off}$=54.2 ms,
$\Delta n$=0.125.

Mixture Example C

80% of basic mixture 3
12% of 4-cyano-3-fluorophenyl 4-(3E-pentenyl)benzoate.
8% of 4-cyano-3 -fluorophenyl 4-(3 -butenyl)benzoate.
cl.p. (N—I) 93° C., $V_{10}$=1.47 V, $t_{on}$=22.4 ms, $t_{off}$=40.8 ms,
$\Delta n$ =0.144.

We claim:
1. A compound of the formula

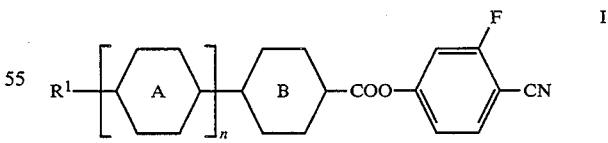

wherein ring A is trans-1,4-cyclohexylene, 1,4-phenylene, pyrimidine-2,5-diyl or trans-1,3-dioxane-2,5-diyl; n is either the integer 0 or 1; ring B is 1,4-phenylene or trans-1,4-cyclohexylene; and $R^1$ has a maximum of 12 carbon atoms and is 3E-alkenyl or when positioned on a saturated ring, $R^1$ also can be 1E-alkenyl; with the proviso that when n is 0, $R^1$ is 3-butenyl or ring B is trans-1,4-cyclohexylene.

2. The compound according to claim 1, wherein $R^1$ has a maximum of 7 carbon atoms.

3. The compound according to claim 2, selected from the group consisting of the formula

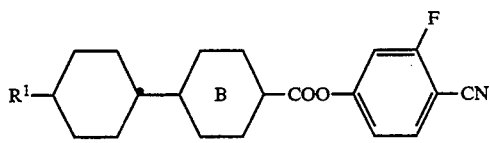

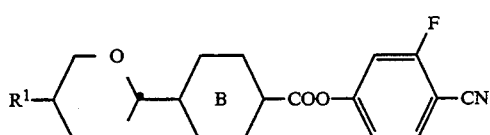

wherein B is 1,4-phenylene.

4. A liquid crystalline mixture having at least two components, wherein at least one component is a compound of the formula

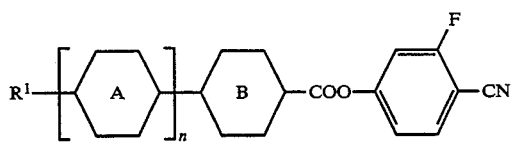

wherein ring A is trans-1,4-cyclohexylene, 1,4-phenylene, pyrimidine-2,5-diyl or trans-1,3-dioxane-2,5-diyl; n is either the integer 0 or 1; ring B is 1,4-phenylene or trans-1,4-cyclohexylene; and $R^1$ has a maximum of 12 carbon atoms and is 3E-alkenyl or when positioned on a saturated ring, $R^1$ also can be 1E-alkenyl; with the proviso that when n is 0, $R^1$ is 3-butenyl or ring B is trans-1,4-cyclohexylene.

5. The liquid crystalline mixture according to claim 4, wherein compound formula I is about 1 to about 50% (weight) of the mixture.

6. The liquid crystalline mixture according to claim 5, wherein compound I is about 5 to about 30% (weight) of the mixture.

7. The liquid crystalline mixture according to claim 5, further comprising at least one compound of the formula

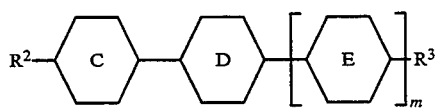

wherein rings C, D and E each independently are 1,4-phenylene, trans-1,4-cyclohexylene or one of these rings also is pyrimidine-2,5-diyl; m is either the integer 0 or 1; ring $R^2$ is alkyl, alkoxyalkyl, 3E-alkenyl, 4-alkenyl or when positioned on trans-1,4-cyclohexylene, $R^2$ also can be 1E-alkenyl; and $R^3$ is cyano, alkyl, alkoxy, alkoxyalkyl, 3E-alkenyl, 4-alkenyl, 2E-alkenyloxy, 3-alkenyloxy or when positioned on trans-1,4-cyclohexylene, $R^3$ also can be 1E-alkenyl wherein alkyl is a straight-chain alkyl of 1 to 12 carbon atoms or a branched-chain alkyl group of 1 to 12 carbon atoms; alkoxy are moieties in which its alkyl portion is as previously defined; and alkenyl is a straight-chain or branched-alkenyl residue of 2-12 carbon atoms.

8. The liquid crystalline mixture according to claim 7, further comprising a compound of the formula

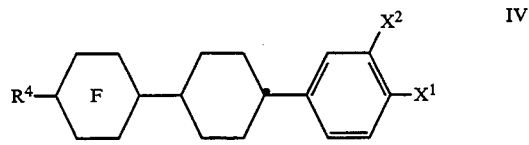

wherein ring F is trans-1,4-cyclohexylene or trans-1,3-dioxane-2,5-diyl; $R^4$ is alkyl, 1E-alkenyl, 3E-alkenyl, 4-alkenyl or alkenyloxy; $X^1$ is fluorine or chlorine; and $X^2$ is hydrogen or fluorine.

9. The liquid crystalline mixture according to claim 8 wherein compound III is present in an amount or about 20 to about 80% (weight) and compound IV is present in an amount of about 5 to about 25% (weight) of the mixture.

10. The liquid crystalline mixture according to claim 9, wherein compound III is present in an amount of about 40 to about 60% (weight) and compound IV is present in an amount of about 10 to about 20% weight of the mixture.

11. An electro-optical cell comprising:
    (a) two plate means;
    (b) a compound disposed between the plate means and having the formula

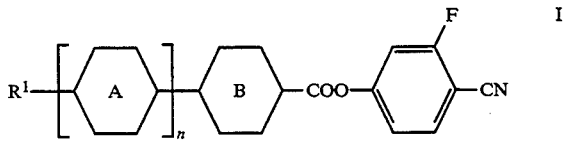

wherein ring A is trans-1,4-cyclohexylene, 1,4-phenylene, pyrimidine-2,5-diyl or trans-1,3-dioxane-2,5-diyl; n is either the integer 0 or 1; ring B is 1,4-phenylene or trans-1,4-cyclohexylene; and $R^1$ has a maximum of 12 carbon atoms and is 3E-alkenyl or when positioned on a saturated ring, $R^1$ also can be 1E-alkenyl; with the proviso that when n is 0, $R^1$ is 3-butenyl or ring B is trans-1,4-cyclohexylene,
    (c) means for applying an electrical potential to said plate means.

* * * * *